United States Patent [19]

Kuncl et al.

[11] Patent Number: 4,918,060

[45] Date of Patent: Apr. 17, 1990

[54] METHOD OF TREATING MYASTHENIA GRAVIS AND RELATED DISEASES

[75] Inventors: Ralph W. Kuncl; Daniel B. Drachman, both of Baltimore, Md.

[73] Assignee: The Johns Hopkins University, Baltimore, Md.

[21] Appl. No.: 92,901

[22] Filed: Sep. 4, 1987

[51] Int. Cl.$^4$ ............................................. A61K 31/70
[52] U.S. Cl. ..................................................... 514/46
[58] Field of Search ..................................... 514/45, 46

[56] References Cited

U.S. PATENT DOCUMENTS

| | | | |
|---|---|---|---|
| 4,148,888 | 4/1979 | Cantoni et al. | 514/46 |
| 4,322,411 | 3/1982 | Vinegar et al. | 514/46 |
| 4,335,040 | 6/1982 | Livingston | 530/427 |
| 4,347,315 | 8/1982 | Krenitsky et al. | 435/87 |

FOREIGN PATENT DOCUMENTS

| | | |
|---|---|---|
| 0010668 | 5/1980 | European Pat. Off. ............ 514/46 |
| 0038567 | 10/1981 | European Pat. Off. |
| 0038568 | 10/1981 | European Pat. Off. |

OTHER PUBLICATIONS

Kuncl et al; Proc. Natl. Acad. Sci. USA, vol. 85, pp. 4032–4036, Jun. 1988; "Inhibition of Methyltransferase Reduces the Turnover of Acetylcholine Receptors".
Fambrough et al; Science, vol. 182, pp. 293–295, Oct. 19, 1973; "Neuromuscular Junction in Myasthenia Gravis: Decreased Acetylcholine Receptors".
Pestronk et al; Brain Research, 412 (1987), pp. 302–310; "Mechanism of Action of Lithium on Acetylcholine Receptor Metabolism in Skeletal Muscle".
Toyka et al; New England Journal of Medicine (reprinted from) 296:125–131 (Jan. 20), 1977; "Myasthenia Gravis-Study of Humoral Immune Mechanisms by Passive Transfer to Mice".
Jerald L. Hoffman; Usdin, Borchardt, Creveling, eds. Transmethylation; pp. 181–186; "Inhibition of S-Adenosyl Sulfur Amino Acid Metabolism: Periodate-Oxidized Nucleosides as Potent Inhibitors of S-Adenosylhomocysteine Hydrolase".
Christian de Duve; Eur. J. Biochem. 137, 391–397 (1983); "Sysosomes Revisted".
Mark Marsh; Biochem. J. (1984), vol. 218, pp. 1–10; "Review Article-The Entry of Enveloped Viruses into Cells by Endocytosis".
Blecher et al; Receptors and Human Disease; Williams & Wilkins, Balto/London, 1981; Chapter 5; Insulin Receptors: Miscellaneous Disorders; pp. 77–94.
Kahn et al; Receptors, Antibodies and Disease, CIBA Foundation Symposium 90, 1982, Pitman, London; "Autoantibodies to Insulin Receptors in Man: Immunological Determinants and Mechanism of Action".
Maddon et al; Cell; vol. 47, pp. 333–348, Nov. 17, 1986; The T4 Gene Encodes the Aids Virus Receptor and is Expressed in the Immune System and the Brain.
Medzihradsky, Regulatory Role for the Immune Complex in Modulation of Phagocytosis by 3-Deazaadenosine, The Journal of Immunology, vol. 133, No. 2, pp. 946–949.
Montgomery et al, Carbocyclic Analogue of 3-Deazaadenosine: A Novel Antiviral Agent Using S-Adenosylhomocysteine Hydrolase as a Pharmacological Target.
Bader et al., 3-Deazaadenosine, an Inhibitor of Adenosylhomocysteine Hydrolase, Inhibits Reproduction of Rous Sarcoma Virus . . . , Virology 89, 494–505 (1978).
Backlund et al., Effects of the S-Adenosylhomocysteine Hydrolase . . . , Eur. Biochem. 160, pp. 245–251 (1986).
Lentz, Binding of Viral Attachment Protein to Host-Cell Receptor: The Achilles Heel of Infectious Viruses, Trends in Pharmacological Sciences, Jul. 1988, vol. 9, No. 7.
M. Blecher et al., Introduction to Receptors, in Receptors and Human Disease, Williams and Wilkins, 1981, pp. 1–23.
Boyle et al, the Chemical Abstracts, 97:107628r (1982).
Finbloom et al, the Chemical Abstracts, 106:17488e (1987).
Medzihradsky et al, the Chemical Abstracts 107:5565a (1987).

*Primary Examiner*—John W. Rollins
*Attorney, Agent, or Firm*—Cushman, Darby & Cushman

[57] ABSTRACT

A method of treating a disorder of receptors involving mediation by endocytosis which comprises administering to a host suffering from said disorder, an effective amount of 3-deazaadenosine or periodate-oxidized adenosine.

3 Claims, No Drawings

METHOD OF TREATING MYASTHENIA GRAVIS AND RELATED DISEASES

The present invention is concerned with the treatment of diseases of receptors mediated by endocytosis. The invention is particularly concerned with the treatment of myasthenia gravis although the treatment of other generally related diseases involving abnormalities of receptors which are mediated by endocytosis is also contemplated.

The work described herein was supported by grants from the National Institute of Health.

Myasthenia gravis is a disease characterized by muscle weakness and fatigability, caused by an autoimmune attack by antibody directed against the acetylcholine receptor (AChR). Such attack results in the blockade and loss of AChRs at neuromuscular junctions.

Myasthenia gravis is most often treated with anticholinesterase agents which function to prolong the action of acetylcholine at neuromuscular junctions. These have temporarily desirable effects (lasting hours), but they do not alter the primary pathophysiology either of autoimmune production of antibody or degradation of the AChR, and they are often insufficient as therapy for many myasthenics.

Another approach to the problem is the use of thymectomy. This procedure, which is now used for most myasthenics from puberty through age 50-60, is effective in a proportion of patients. However, the procedure requires major surgery and has a latency of months or years to providing its beneficial effect towards promoting remission.

Steroids and other immunosuppressive drugs are also used for treating myasthenia gravis. These can be effective in many patients but this is accomplished at the cost of general immunosuppression. Additionally, this treatment may have a latency of months prior to any benefit. There are also significant risks and substantial degrees of toxicity involved in using certain of these materials, notably prednisone, azathioprine, and cyclosporin A. Plasmapheresis may be used as an adjunct to immunosuppressive drugs to provide a shorter-term benefit. However, this treatment is costly.

Thus, while methods of treating myasthenia gravis are known, these methods generally suffer from one or more significant disadvantages. Accordingly, the principal object of the invention is to provide a different method of treating myasthenia gravis which should be free from, or at least minimize, prior art disadvantages.

The invention is based on the concept of treating myasthenia gravis or related disorders by reducing the accelerated endocytosis of acetylcholine receptors. According to the invention, this is accomplished by using methylation inhibitor drugs such as 3-deazaadenosine (3DZA) or periodate-oxidized adenosine (POA).

It is believed that the present invention represents the first effort to treat myasthenia gravis or the like by dealing directly with the accelerated turnover of AChR itself. This turnover of AChR is believed to be a key pathophysiologic mechanism in myasthenia gravis that is important in affecting disease severity.

the use of 3DZA, according to the invention, is believed to reduce the endocytosis of membrane receptors, particularly when their turnover is accelerated by antibody. 3DZA inhibits S-adenoxylhomocysteine (SAH) hydrolase, causing accumulation of SAH, thus causing competitive inhibition of phospholipid methylation reactions and resultant changes in membrane properties. 3DZA inhibits endocytosis in fibroblasts and it has been found to do so potently in skeletal muscle.

A particular advantage of 3DZA is its remarkable lack of toxicity in animals. This means that the compound may be effectively used at dosages far below those causing any toxicity. A second particular advantage of 3DZA is that its rapid action on AChR turnover predicts a rapid benefit from therapy within 1-2 weeks. Another advantage is that the drug has immunosuppressive properties when used at higher doses, which could be of added benefit in autoimmune disease. 3DZA is currently in trial for use in treating rheumatoid arthritis.

The invention is more fully illustrated by the following:

(i) In muscle cell culture a combination of drugs that inhibit phospholipid methylation (adenosine, homocysteine, and erythro-9-(2-hydroxy-3-nonyl)-adenine significantly reduces the normal turnover of AChRs and also reduces the accelerated endocytosis and loss of AChRs that is triggered by myasthenic anti-AChR antibody.

(ii) In muscle culture, 3DZA also potently reduces the turnover of AChRs and inhibits the accelerated endocytosis of AChRs that is triggered by anti-AChR antibody. The effect occurs within hours and lasts days. The effect occurs without toxicity to cells, as measured by cell morphology and protein synthesis.

(iii) In muscle cell culture, POA also reduces the turnover of AChRs and inhibits the accelerated endocytosis of AChRs that is triggered by anti-AChR antibody. It does so with the same potency as does 3DZA, again without any nonspecific toxicity to protein synthesis.

(iv) Tests have been carried out in an animal model in which human myasthenic antibody, passively transferred, induces myasthenia in mice. Mice so subjected to the transferred antibody, rapidly lose AChRs at neuromuscular junctions because of accelerated turnover. However, it has been found that 3DZA significantly reduces this loss of receptors within 1 week of therapy. It is noted in this regard that the probability (p) of such a large effect occurring by chance alone is $<0.05$.

The therapeutic effect of 3DZA in passively transferred myasthenia gravis is shown by the following data:

TABLE 1

| Experimental Condition | Number AChRS per Neuromuscular junction $\times 10^7$ ($\pm$ standard error of mean) |
|---|---|
| Control immunoglobulin | 1.68 ± 0.11 |
| 3DZA only | 2.31 ± 0.29 |
| Myasthenic immunoglobulin | 0.67 ± 0.10 |
| Myasthenic immunoglobulin plus 3DZA | 1.05 ± 0.10 |

As is evident, use of the 3DZA results in a significant increase in the number of AChRs per neuromuscular junction. This increase is of such a magnitude as to be physiologically important for the prevention of symptoms in myasthenia gravis. In particular, the indicated endocytosis-inhibiting properties of 3DZA, as illustrated by the above data, indicate that 3DZA would be effecitve in the treatment of acquired myasthenia gravis and congenital myasthenia gravis. Suppression of endocytosis also indicates more general uses in the treatment of other disorders of other receptors mediated by endocytosis (e.g. certain forms of diabetes). Its effect in inhibiting receptor-mediated endocytosis could also prove beneficial in certain infections (where viruses enter the cells by endocytosis during the process of infection), and in the treatment of certain cancers, where cell growth requires receptor-mediated endocytosis of growth factors.

It is contemplated that treatment herein using 3DZA or POA would be carried out by administering the 3DZA or POA in any conventional way to warm-blooded animals or mammals, including humans. Suitable composition forms which are visualized include tablets, pills, sterile injectable solutions, etc. The 3DZA or POA may be formulated for administration with conventional carriers or excipients as will be understood by those in the art. It is believed that such compositions would comprise from 0.05 to 10% by weight of the 3DZA or POA although amounts outside this range may also be used. Dosages will necessarily vary on other factors, e.g. the weight of the host being treated. It is contemplated, however, that an effective dosage of 0.001% to 0.5% of 3DZA or POA based on the weight of the host, and given once or twice a day will provide effective treatment of myasthenia gravis.

It will be recognized that various modifications may be made in the invention as described above. For example, the 3DZA or POA may be used in combination with other drugs which are known to be effective in the treatment of my or other diseases. Accordingly, the scope of the invention is defined in the following claims wherein:

We claim:

1. A method of treating endocytosis of intrinsic membrane receptors in a warm-blooded animal in need of such treatment, which comprises administering to the warm-blooded animal an amount of 3-deazaadenosine which is effective to reduce the endocytosis of said membrane receptors.

2. The method of claim 1, wherein the administration of 3-deazaadenosine is used to reduce endocytosis in the treatment of myasthenia gravis.

3. The method of claim 1, wherein the membrane receptors are acetylcholine receptors.

* * * * *